United States Patent [19]
Tanaka et al.

[11] Patent Number: 6,130,332
[45] Date of Patent: *Oct. 10, 2000

[54] METHOD OF ALKYLATING TRIAZINE DERIVATIVES

[75] Inventors: Norio Tanaka; Kenichi Mizusawa; Makoto Ishikawa; Yasuo Fukue; Isao Hashiba, all of Funabashi; Yoshihisa Watanabe, Joyo, all of Japan

[73] Assignee: Nissan Chemical Industries, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/737,712
[22] PCT Filed: May 9, 1995
[86] PCT No.: PCT/JP95/00881
  § 371 Date: Feb. 7, 1997
  § 102(e) Date: Feb. 7, 1997
[87] PCT Pub. No.: WO95/30662
  PCT Pub. Date: Nov. 16, 1995

[30] Foreign Application Priority Data

May 10, 1994 [JP] Japan .................................... 6-96594
Nov. 15, 1994 [JP] Japan .................................. 6-280370

[51] Int. Cl.[7] ...................... C07D 251/16; C07D 251/18; C07D 251/42; C07D 251/48
[52] U.S. Cl. .......................... 544/194; 544/196; 544/200; 544/204; 544/205; 564/398
[58] Field of Search .................... 544/194, 196, 544/200, 204, 205; 564/398

[56] References Cited

U.S. PATENT DOCUMENTS

| | | | |
|---|---|---|---|
| 3,522,309 | 7/1970 | Kirby et al. | 564/463 |
| 4,207,260 | 6/1980 | Imai | 564/463 |
| 4,261,926 | 4/1981 | Ross et al. | 564/305 |

FOREIGN PATENT DOCUMENTS

| | | | |
|---|---|---|---|
| 0 212 303 | 3/1967 | European Pat. Off. | |
| 0 014 998 | 9/1980 | European Pat. Off. | |
| 0 142 868 | 5/1985 | European Pat. Off. | |
| 0 323 573 | 7/1989 | European Pat. Off. | |
| 0 427 572 A1 | 5/1991 | European Pat. Off. | |
| 0 711 760 A1 | 5/1996 | European Pat. Off. | |
| 3528262 | 2/1987 | Germany | 564/398 |
| 47-17784 | 7/1972 | Japan . | |
| 0753740 | 8/1956 | United Kingdom | 564/398 |
| 1 369 917 | 10/1974 | United Kingdom . | |
| WO 95/03287 | 2/1995 | WIPO . | |

OTHER PUBLICATIONS

Hudlicky, Milos., Reductions in Organic Chemistry, 4–8, 10–12,40,49, 62–63,66–69 1984.

Paquette L.A., Encyclopedia of Reagents for Organic Synthesis1257–1258, 3785,4401–4402, 1995.

Fieser and Fieser, Reagents for Organic Synthesis, vol. 1, p. 140, 1965.

H. Snyder, "Preparation of Amines by Reductive Alkylation",*Organic Reactions*, vol. IV, pp. 175–255, (1979).

*Primary Examiner*—Mukund J. Shah
*Assistant Examiner*—V. Balasubramanian
*Attorney, Agent, or Firm*—Oliff & Berridge, PLC

[57] ABSTRACT

The object of the present invention is to provide a method for producing substituted-1,3,5-triazine derivatives at high yield, in which at least one of carbon atoms in the ring thereof is substituted by a secondary amine group having at leat one of alkyl groups. The method of the present invention is a method for alkylation of 1,3,5-triazine derivatives, characterized by reacting 1,3,5-triazine derivatives (melamines, melamine derivatives, various kinds of guanaminde derivatives, etc.) which has at least one or more amino groups or mono-substituted amino groups on carbon atom of the ring thereof, with aldehydes or ketones alcohols in the presence of a catalyst of a metal of group VII and/or group VIII in the periodic table and a hydrogen-containing gas to alkylate said at least one of amino groups or mono-substituted amino groups. These derivatives are widely used as intermediates of fine chemicals such as agricultural chemicals, medications, dyestuffs, paints and the like and are widely used resin materials and as flame-retardant materials.

14 Claims, No Drawings

METHOD OF ALKYLATING TRIAZINE DERIVATIVES

TECHNICAL FIELD

The present invention relates to a method for alkylation of 1,3,5-triazine derivatives which comprises reacting the 1,3,5-triazines having at least one or more amino groups or mono-substituted amino groups with aldehydes or ketones in the presence of a catalyst of a metal of group VII and/or group VIII in the periodic table and hydrogen-containing gas and alkylating said at least one or more amino groups or mono-substituted amino groups.

The substituted 1,3,5-triazine derivatives obtained by alkylation of the amino group(s) or mono-substituted amino group(s) on the carbon atom(s) of the triazine ring of the 1,3,5-triazine derivatives in the present invention are a group of useful compounds which are widely used as intermediates of fine chemicals such as agricultural chemicals, medications, dyestuffs, paints and the like, as resin materials, among others, as aminoplasts-forming components, and as flame-retardant materials.

TECHNICAL BACKGROUND

As a method for producing substituted triazines, various methods have been known so far. It is reported, for example, a method in which a compound of the formula (III)

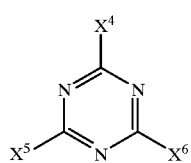

(III)

wherein $X^4$ and $X^5$ each represent an diethylamino group and $X^6$ represents an ethylamino group or $X^4$ and $X^5$ represent an amino group and $X^6$ represents an ethylamino group or diethylamino group is produced by the reaction of 2-chloro-1,3,5-triazine with ethylamine (J. Amer. Chem. Soc., vol. 73, p. 2984, 1951).

It is reported a method in which a compound of the formula (III) wherein $X^4$, $X^5$ and $X^6$ each represent an ethylamino group is produced by the reaction of 2,4,6-trimethylthio-1,3,5-triazine with ethylamine (Chem. Ber., vol. 18, p. 2755, 1885).

It is reported a method in which a compound of the formula (III) wherein $X^4$ represents an amino group, $X^5$ represents an amino group or an octylamino group, and $X^6$ represents an octylamino group is produced by the reaction of 2,4,6-triamino-1,3,5-triazine with octylamine hydrochloride (U.S. Pat. No. 2,228,161, 1941).

It is reported a method in which a compound of the formula(III) wherein $X^4$ represents a phenyl group, and $X^5$ and $X^6$ each represent a butylamino group is produced by the reaction of 2-phenyl-4,6-diamino-1,3,5-triazine with butylamine (U.S. Pat. No. 2,385,766, 1945). Further, 2,4,6-1,3,5-triazine derivatives produced from cyanuric chloride are used as a flame retardant of a thermoplastic polymer (Japanese Patent Application Laid-Open No. Hei 3-1215564). Specific examples of the derivatives described in this Japanese Patent Application Laid-open No. Hei 3-215564 are as follows as a part thereof.

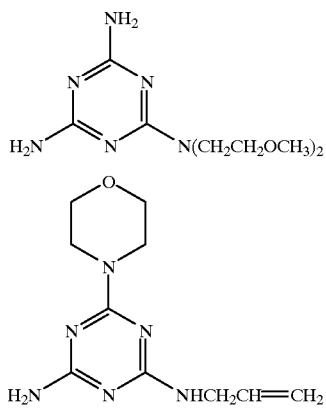

Examples of reaction of aminotriazines with carbonyl compounds such as aldehydes or ketones are represented by the reaction example in which hydroxymethylation was conducted by melamine and an aqueous formalin solution under the weakly alkali condition. (J. Amer. Chem. Soc., vol. 69, p. 599, 1947).

The method described in J. Amer. Chem. Soc., vol. 73, p. 2984, 1954 requires a condensation agent in an amount of more than a stoichiometrical amount in many cases and causes formation of by-products such as salts and the like which is often industrially problematic. The method described in Chem. Ber., vol. 18, p. 2755, 1885 causes formation of by-products such as sulfur compounds and the like which is often industrially problematic. The methods described in U.S. Pat. No. 2,228,161 (1941) and U.S. Pat. No. 2,385,766 (1945) require high temperatures in the reaction. Besides, the former method causes formation of by-product ammonium chloride. Any of the above-mentioned methods conduct the substitution reaction with the leaving group by using substituted amines which are not said to be industrially inexpensive, and this is one of the reasons that substituted triazines cannot be supplied at low costs.

In the reactions of amino trizines with carbonyl compounds such as aldehydes or ketones, the reactivity of amino group in the triazine rings is low. Therefore, as described in J. Amer. Chem. Soc., vol. 69, p. 599, 1947, it is general to carry out the hydroxymethylation by the reaction with formaldehyde which has high reactivity with melamines. In a case of the reaction with other carbonyl compounds, especially, with aldehydes, it has been known such a reaction that an equilibrium mixture of a raw material and a hydroxyalkylated compound is obtained and its product is unstable or a reaction under dehydration-condensation with further aminotriazines is easily conducted to obtain polynucleic compounds.

DISCLOSURE OF THE INVENTION

The present inventors have assiduously conducted investigations to solve the problems associated with the prior art, and have consequently reached to the completion of the present invention, in which various kinds of aldehyde derivatives or ketone derivatives which are industrially inexpensive are reacted with amino groups or mono-substituted amino groups in the triazine nucleus in the presence of a catalyst of metal of group VIII in the periodic table and a hydrogen containing gas to introduce an alkyl group into said amino group or mono-substituted amino group at high yield and only water is formed as a by-product.

Further, since the substituted 1,3,5-triazine derivatives obtained by the method of the present invention notably inhibit the inter-polymolecular association by hydrogen-bonding inherent in aminotriazines, solubility in solvents is improved. Further, as melting points are simultaneously fallen, compatibility with other organic compounds are improved. This is explained by referring to melamine for example. After the completion of the reaction, unreacted melamine is mostly crystallized and precipitated in a solvent used in the reaction, and is separated through filtration or the like. Meanwhile, almost of the reaction products are dissolved in the solvent. Accordingly, the method of the present invention is also excellent in terms of separation and purification of the reaction product.

It is an object of the present invention to provide a method for alkylation of 1,3,5-triazine derivatives, which comprises alkylating amino groups or mono-substituted amino groups on carbon atoms of a 1,3,5-triazine ring by using carbonyl compounds such as aldehydes or ketones, whereby substituted 1,3,5-triazine derivatives which are a group of useful compounds and which are widely used as intermediates of fine chemicals such as agricultural chemicals, medications, dyestuffs, paints and the like, as resin materials and as flame-retardant materials can easily be produced in high yields.

That is, the present invention relates to a method for alkylation of 1,3,5-triazine derivatives which comprises reacting 1,3,5-triazine derivative which has at least one or more amino groups or mono-substituted amino groups on carbon atom of the ring with an aldehyde or a ketone in the presence of a catalyst of a metal of group VII and/or group VIII in the periodic table and a hydrogen-containing gas to alkylate at least one or more amino groups or mono-substituted amino groups.

Alkylating amino groups or mono-substituted amino groups in the present invention means that amino groups are converted into mono- or di-alkylamino groups or mono-substituted amino groups are converted into di-alkylamino groups which is further alkylated.

The present invention will be described in more detail below. The 1,3,5-triazine derivatives having at least one or more amino groups or mono-substituted amino groups, which are starting materials of the present invention, are represented by formula (I).

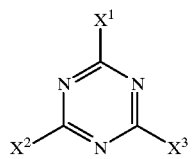

(I)

[wherein at least one of $X^1$, $X^2$ and $X^3$ independently represents $NHR^1$ {in which $R^1$ represents a hydrogen atom, a $C_{1-20}$ alkyl group (said alkyl group is optionally substituted with a halogen atom, a trifluoromethyl group, a hydroxyl group, a $C_{1-6}$ alkoxy group, a $C_{1-6}$ haloalkoxy group, an aryloxy group, a $C_{2-7}$ alkoxycarbonyl group, a $C_{2-7}$ acyloxy group, an amino group, a $C_{1-8}$ monoalkylamino group, a $C_{2-12}$ dialkylamino group, a phenyl group (said phenyl group is optionally substituted with a halogen atom, a $C_{1-6}$ alkyl group, a hydroxyl group or a $C_{1-6}$ alkoxy group)) or a $C_{2-20}$ alkenyl group (said alkenyl group is optionally substituted with a halogen atom, a trifluoromethyl group, a hydroxyl group, a $C_{1-6}$ alkoxy group, a $C_{1-6}$ haloalkoxy group, an aryloxy, a $C_{2-7}$ alkoxycarbonyl group, a $C_{2-7}$ acyloxy group, an amino group, a $C_{1-8}$ monoalkylamino group, $C_{2-12}$ dialkylamino group or a phenyl group (said phenyl group is optionally substituted with a halogen atom, a $C_{1-6}$ alkyl group, a hydroxyl group or a $C_{1-6}$ alkoxy group))}, and $X^1$, $X^2$ and $X^3$ which are not $NHR^1$ independently represent $NR^2R^3$ {in which $R^2$ and $R^3$ independently represent a $C_{1-20}$ alkyl group (said alkyl group is optionally substituted with a halogen atom, a trifluoromethyl group, a hydroxyl group, a $C_{1-6}$ alkoxy group, a $C_{1-6}$ haloalkoxy group, an aryloxyl group, a $C_{2-7}$ alkoxycarbonyl group, a $C_{2-7}$ acyloxy group, an amino group, a $C_{1-8}$ monoalkylamino group, a $C_{2-12}$ dialkylamino group or a phenyl group (said phenyl group is optionally substituted with a halogen atom, a $C_{1-6}$ alkyl group, a hydroxyl group or a $C_{1-6}$ alkoxy group)), a $C_{2-20}$ alkenyl group (said alkenyl group is optionally substituted with a halogen atom, a trifluoromethyl group, a hydroxyl group, a $C_{1-6}$ alkoxy group, a $C_{1-6}$ haloalkoxy group, an aryloxyl group, a $C_{2-7}$ alkoxycarbonyl group, a $C_{2-7}$ acyloxy group, an amino group, a $C_{1-8}$ monoalkylamino group, a $C_{2-12}$ dialkylamino group or a phenyl group (said phenyl group is optionally substituted with a halogen atom, a $C_{1-6}$ alkyl group, a hydroxyl group or a $C_{1-6}$ alkoxy group)), or $R^2$ and $R^3$ may together form —$(CH_2)_{2-5}$—, —$CH_2CH_2$—$(C_{1-8}$ alkyl)$N$—$CH_2CH_2$— or $CH_2CH_2$—$O$—$CH_2CH_2$— in which an alkylene chain is optionally substituted with one or two $C_{1-8}$ alkyl groups}, a $C_{1-20}$ alkyl group {said alkyl group is optionally substituted with a halogen atom, a hydroxyl group, a $C_{1-6}$ alkoxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}, a $C_{2-20}$ alkenyl group {said alkenyl group is optionally substituted with a halogen atom, a hydroxyl group, a $C_{1-6}$ alkoxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}, a phenyl group {said phenyl group is optionally substituted with a $C_{1-6}$ alkyl group, a halogen atom, a hydroxyl group, a $C_{1-6}$ alkoxy group, an aryloxy group, a $C_{2-10}$ acyloxy group, a carboxyl group, a $C_{2-7}$ alkoxycarbonyl group, a $C_{2-10}$ acyl group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}, a halogen atom, a $C_{1-10}$ alkoxy group {said alkoxy group is optionally substituted with a halogen atom, a hydroxyl group, a $C_{1-6}$ alkoxy group, an aryloxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)), or a $C_{1-10}$ alkylthio group {said alkylthio group is optionally substituted with a halogen atom, a hydroxyl group, a $C_{1-6}$ alkoxy group, an aryloxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group, an aryl group (said aryl group is optionally substituted with a halogen atom, a $C_{1-6}$ alkyl group, a hydroxyl group or a $C_{1-6}$ alkoxy group)).

In the specification and claims of the present application, the expression "which is optionally substituted with a substituent . . . " means "which may be substituted with one or more of substituents which are the same or different and which are selected from substituents . . . ".

Preferable are 1,3,5-triazine derivatives of the formula (I) of the 1,3,5-triazine derivatives in which $R^1$ of $NHR^1$ represents a hydrogen atom, a $C_{1-20}$ alkyl group {said alkyl group is optionally substituted with a halogen atom, a hydroxyl group, a $C_{1-6}$ alkoxy group, a phenyl group (said phenyl group is optionally substituted with a halogen atom, a $C_{1-6}$ alkyl group, a hydroxyl group or a $C_{1-6}$ alkoxy group)}, a $C_{2-20}$ alkenyl group {said alkenyl group is optionally substituted with a halogen atom, a hydroxyl group, a $C_{1-6}$ alkoxy group or a phenyl group (said phenyl group is optionally substituted with a halogen atom, a $C_{1-6}$ alkyl group, a hydroxyl group or a $C_{1-6}$ alkoxy group)}, and $X^1$, $X^2$ and $X^3$ which are not $NHR^1$ independently represent $NR^2R^3$ {in which $R^2$ and $R^3$ independently represent a $C_{1-20}$ alkyl group {said alkyl group is optionally substituted with a halogen atom, a hydroxyl group, a $C_{1-6}$ alkoxy group or a phenyl group (said phenyl group is optionally substituted with a halogen atom, a $C_{1-6}$ alkyl group, a hydroxyl group, or a $C_{1-6}$ alkoxy group)}, or a $C_{2-20}$ alkenyl group {said alkenyl group is optionally substituted with a halogen atom, a $C_{1-6}$ alkoxy group or a phenyl group (said phenyl group is optionally substituted with a halogen atom, a $C_{1-6}$ alkyl group, a hydroxyl group or a $C_{1-6}$ alkoxy group)}, or $R^2$ and $R^3$ may together form —$(CH_2)_{3-5}$—, —$CH_2$ $CH_2$—$(C_{1-8}$ alkyl)N—$CH_2CH_2$— or —$CH_2CH_2$—O— $CH_2CH_2$— in which an alkylene chain is desirably substituted with one or two $C_{1-8}$ alkyl groups}, a $C_{1-20}$ alkyl group {said alkyl group is optionally substituted with a halogen atom, a hydroxyl group, a $C_{1-6}$ alkoxy group or an aryl group (said aryl group is optionally substituted with a halogen atom, a $C_{1-6}$ alkyl group, a hydroxyl group or a $C_{1-6}$ alkoxy group)}, a phenyl group (said phenyl group is optionally substituted with a $C_{1-6}$ alkyl group, a halogen atom, a hydroxyl group, a $C_{1-6}$ alkoxy group or an aryl group (said aryl group is optionally substituted with a halogen atom, a $C_{1-6}$ alkyl group, a hydroxyl group or a $C_{1-6}$ alkoxy group)), a halogen atom, or a $C_{1-10}$ alkoxy group {said alkoxy group is optionally substituted with a halogen atom, a hydroxyl group, a $C_{1-6}$ alkoxy group, or an aryl group (said aryl group is optionally substituted with a halogen atom, a $C_{1-6}$ alkyl group, a hydroxyl group or a $C_{1-6}$ alkoxy group)}.

More preferable 1,3,5-triazine derivatives of the formula (I) are 1,3,5-triazine derivatives of the formula (I) in which $R^1$ of $NHR^1$ represents a hydrogen atom or a $C_{1-20}$ alkyl group (said alkyl group is optionally substituted with a hydroxyl group, a $C_{1-6}$ alkoxy group or a phenyl group), and $X^1$, $X^2$ and $X^3$ which are not $NHR^1$ independently represent $NR^2R^3$ {in which $R^2$ and $R^3$ independently represent a $C_{1-20}$ alkyl group (said alkyl group is optionally substituted with a hydroxyl group, a $C_{1-6}$ alkoxy group or a phenyl group), or $R^2$ and $R^3$ may together form —$(CH_2)_{4-5}$—, —$CH_2CH_2$—$(C_{1-8}$ alkyl)N—$CH_2CH_2$— or —$CH_2CH_2$— O—$CH_2CH_2$— in which an alkylene chain is optionally substituted with one or two $C_{1-8}$ alkyl groups)}, a $C_{1-20}$ alkyl group,
a phenyl group, or
a $C_{1-10}$ alkoxy group.

All of the 1,3,5-triazine derivatives having materials which do not react under the reaction conditions of the present invention can be used in the reaction as mentioned above. Melamine derivatives and guanamine derivatives can be mentioned as industrially available intermediates (these are used mainly as a main component or a modifier of thermosetting resins or crosslinking agents for baking paints, and a method of producing the same is detailed in "s-Triazines and Derivatives, The Chemistry of Heterocyclic Compounds, E. M. Smolin and L. Rapoport., Interscience Publishers Inc., New York 1959").

The aldehydes or ketones which can be used in the present invention are aldehyde derivatives or ketone derivatives of the formula (II):

(II)

[wherein $R^4$ and $R^b$ independently represent a hydrogen atom, a $C_{1-20}$ alkyl group {said alkyl group optionally substituted with a halogen atom, a hydroxyl group, a $C_{1-6}$ alkoxy group, a $C_{1-6}$ haloalkoxy group, a $C_{2-7}$ alkoxycarbonyl group, a $C_{2-7}$ acyloxy group or a phenyl group (said phenyl group is optionally substituted with a halogen atom, a $C_{1-6}$ alkyl group, a hydroxyl group or a $C_{1-6}$ alkoxy group)}, a $C_{2-20}$ alkenyl group {said alkenyl group is optionally substituted with a halogen atom, a hydroxyl group, a $C_{1-6}$ alkoxy group, a $C_{1-6}$ haloalkoxy group, a $C_{2-7}$ alkoxycarbonyl group, a $C_{2-7}$ acyloxy group or a phenyl group (said phenyl group is optionally substituted with a halogen atom, a $C_{1-6}$ alkyl group, a hydroxyl group or a $C_{1-8}$ alkoxy group)} or $R^4$ and $R^5$ may together form an alkylene group: —$(CH_2)_{3-5}$—].

Preferable are aldehydes or ketones of formula (II) are aldehyde derivatives or ketone derivatives wherein $R^4$ and $R^5$ independently represent a hydrogen atom or a $C_{1-20}$ alkyl group (said alkyl group is optionally substituted with a halogen atom; a hydroxyl group, a $C_{1-6}$ alkoxy group or a phenyl group) or a $C_{2-20}$ alkenyl group (said alkenyl group is optionally substituted with a halogen atom, a hydroxyl group, a $C_{1-6}$ alkoxy group or a phenyl group), or $R^4$ and $R^5$ may together form an alkylene group: —$(CH_2)_{3-5}$—.

More preferable aldehydes or ketones of the formula (II) are aldehyde derivatives or ketone derivatives wherein $R^4$ and $R^5$ independently represent a hydroxyl group or a $C_{1-20}$ alkyl group (said alkyl group represents a halogen atom, a hydroxyl group, a $C_{1-6}$ alkoxy group or a phenyl group), or $R^4$ and $R^5$ may together form an alkylene group: —$(CH_2)_{3-5}$—.

Of these derivatives, industrially available are formaldehyde, acetaldehyde, propionaldehyde, n-butyraldehyde, n-pentylaldehyde, n-hexyl aldehyde, n-octanal, n-nonanal, 2-ethyl hexyl aldehyde, cyclohexylaldehyde, benzaldehyde, acetone, methyl ethyl ketone, methyl isobutyl ketone, cyclopentanone, cyclohexanone and acetophenone.

A catalyst of metals of group VII and group VIII in the periodic table which is used in the present invention includes catalysts of rhenium, iron, cobalt, nickel, ruthenium, rhodium, palladium, osmium, iridium, and platinum. For example, complex catalysts of the above-mentioned. elements, these elements-carried catalysts or the like can be mentioned. Of these elements, nickel, ruthenium, rhodium, palladium, and platinum are preferable. The complex catalyst of nikel, ruthenium, palladium or platinum or these element-carried catalysts are especially preferable. The catalyst used in the present invention is illustrated more specifically below.

Examples of the rhenium catalyst active carbon-carried rhenium catalyst, alumina-carried rhenium catalyst and rhenium heptoxide.

Examples of the iron catalyst include Raney iron or complex catalysts such as pentacarbonyliron, dodecacarbonyltriiron, dichlorobis(triphenylphosphine)iron, tetracarbonyl(triphenyl-phosphine)iron and tricarbonylbis(triphenylphosphine)iron.

Examples of the cobalt catalyst include Raney cobalt or complex catalysts such as octacarbonyldicobalt, dodecacarbonyltricobalt and chlorotris(triphenylphosphine)cobalt.

Examples of the nickel catalyst include solid or element-carried catalysts such as Raney nickel, nickel-carried silica, nickel-carried alumina, and nickel-carried carbon; complex catalysts such as dichlorobis(triphenylphosphine)nickel, tetrakis(triphenylphosphine)nickel and tetrakis(triphenylphosphite)nickel; nickel chloride; and nickel oxide.

Examples of the ruthenium catalyst include catalysts such as ruthenium-carried silica, ruthenium-carried alumina and ruthenium-carried carbon; complex catalysts such as pentacarbonylruthenium, dodecacarbonyltriruthenium, tetrahydridododecacarbonyltetraruthenium, dihydrido(dinitrogen)tris(triphenylphosphine)ruthenium, dicarbonyltris(triphenylphosphine)ruthenium, tetracarbonyl(trimethylphosphite)ruthenium, pentakis(trimethylphosphite)ruthenium, tris(acetylacetonato) ruthenium, diacetatodicarbonylbis(triphenylphosphine)ruthenium, dichlorobis(chlorotricarbonyl)ruthenium, carbonylchlorohydridotris(triphenylphosphine)ruthenium, tetrahydridotris(triphenylphosphine)ruthenium, acetatohydridotris(triphenylphosphine)ruthenium, dichlorobis(acetonitrile)bis(triphenylphosphine)ruthenium, ruthenocene, bis(pentamethylcyclopentadienyl)ruthenium, dichloro(pentamethylcyclopentadienyl)ruthenium, chloro(cyclopentadienyl)bis(triphenylphosphine)ruthenium, hydrido(cyclopentadienyl)bis(triphenylphosphine)ruthenium, chlorocarbonyl(cyclopentadienyl)ruthenium, hydrido(cyclopentadienyl)(1,5-cyclooctadiene)ruthenium, chloro(cyclopentadienyl)(1,5-cyclooctadiene)ruthenium, dihydridotetrakis(triphenylphosphine)ruthenium, cyclooctatriene(cyclooctadiene)ruthenium, chlorohydridotris(triphenylphosphine)ruthenium, tricarbonylbis(triphenylphosphine)ruthenium, tricarbonyl(cyclooctatetraene)ruthenium, tricarbonyl(1,5-cyclooctadiene)ruthenium and dichlorotris(triphenylphosphine)ruthenium; ruthenium chloride; and ruthenium oxide and ruthenium black.

Examples of the palladium catalyst include solid or element-carried catalysts such as Raney palladium, palladium-carried silica, palladium-carried alumina, palladium-carried carbon, palladium-carried barium sulfate, palladium-carried zeolite and palladium-carried silica-alumina; complex catalysts such as dichlorobis(triphenylphosphine)palladium, dichlorobis(trimethylphosphine)palladium, dichlorobis(tributylphosphine)palladium, bis(tricyclohexylphosphine)palladium, tetrakis(triethylphosphite)palladium, bis(cycloocta-1,5-diene)palladium, tetrakis(triphenylphosphine)palladium, dicarbonylbis(triphenylphosphine)palladium, dicarbonyltris(triphenylphosphine)palladium, dichlorobis(benzonitrile)palladium and dichloro(1,5-cyclooctadiene)palladium; palladium chloride; and palladium oxide.

Examples of the rhodium catalyst include catalysts such as rhodium-carried silica, rhodium-carried alumina, and rhodium-carried carbon; complex catalysts such as chlorotris(triphenylphosphine)rhodium, hexadecacarbonylhexarhodium, dodecacarbonyltetrarhodium, dichlorotetracarbonylrhodium, hydridotetracarbonylrhodium, hydrocarbonyltris(triphenylphosphine)rhodium, hydridotetrakis(triphenylphosphine)rhodium, dichlorobis(cyclooctadiene)dirhodium, dicarbonyl(pentamethylcyclopentadienyl)rhodium, cyclopentadienylbis(triphenylphosphine)rhodium and dichlorotetrakis(allyl)dirhodium; rhodium chloride; and rhodium oxide.

Examples of the platinum catalyst include catalysts such as platinum-carried silica, platinum-carried alumina, and platinum-carried carbon; complex catalysts such as dichlorobis(triphenylphosphine)platinum, dichlorobis(trimethylphosphine)platinum, dichlorobis(tributylphosphine)platinum, tetrakis(triphenylphosphine)platinum, tetrakis(triphenylphosphite)platinum, tris(triphenylphosphine)platinum, dicarbonylbis(triphenylphosphine)platinum, carbonyltris(triphenylphosphine)platinum, cis-bis(benzonitrile)dichloroplatinum, and bis(1,5-cyclooctadiene)platinum; platinum chloride; and platinum oxide (Adams catalyst) and platinum black.

Preferable groups of the catalysts used in the methods of the present invention are as follows.

(1) Method in which the catalysts of metals of group VII in the periodic table are rhenium catalysts.

(2) Method of the above group (I) in which the rhenium catalyst is an element-carried catalyst.

(3) Method in which the catalysts of metals of group VIII in the periodic table are at least one catalyst selected from iron, cobalt, nickel, ruthenium, rhodium, palladium, osmium, iridium and platinum catalysts.

(4) Method of the above group (3) in which the catalysts of metals of group VIII in the periodic table are at least one catalyst selected from cobalt, nickel, ruthenium, rhodium, palladium and platinum catalysts.

(5) Method of the above group (4) in which the catalysts of metals of group VIII in the periodic table are at least one catalyst selected from nickel, ruthenium, palladium and platinum catalysts.

(6) Method of the above groups (3), (4) and (5) in which the catalyst is complex catalyst.

(7) Method of the above groups (3), (4) and (5) in which the catalyst is element-carried catalyst.

(8) Method of the above group (2) or (7) in which the carrier of the element-carried catalysts are silica, alumina, zeolite or carbon.

The above-mentioned catalysts may be used either singly or in combination.

The amount of the catalyst of group VIII in the periodic table is usually between 0.0001 and 20 mol %, preferably between 0.0001 and 10 mol % based on the triazine derivatives of formula (I).

A ligand can be added to the above-mentioned catalysts if necessary. Examples of the ligand include monodentate or multidentate tertiary phosphines such as trimethylphosphine, triethylphosphine, tributylphosphine, triphenylphosphine, tris(p-tolyl)phosphine, tris(2,6-dimethylphenyl)phosphine, sodium diphenylphosphinobenzene-3-sulfonate, bis(3-sulfonatophenyl)phosphinobenzene sodium salt, 1,2-bis(diphenylphosphino)ethane, 1,3-bis(diphenylphosphino)propane, 1,4-bis(diphenylphosphino)butane and tris(3-sulfonatophenyl)phosphine sodium salt; phosphorous esters such as triethyl phosphate, tributyl phosphate, triphenyl phosphite and tris(2,6-dimethylphenyl) phosphite; phosphonium salts such as triphenylmethylphosphonium iodide, triphenylmethylphosphonium bromide, triphenylmethylphosphonium chloride, triphenylallylphosphonium iodide, triphenylallylphosphonium bromide, triphenylallylphosphonium chloride, tetraphenylphosphonium iodide, tetraphenylphosphonium bromide, and tetraphenylphosphonium chloride; phosphate (phosphoric esters) such as triphenyl phosphate, trimethyl phosphate, triethyl phosphate, and triallyl phosphate; unsaturated hydrocarbons such as cyclooctadiene, and cyclopentadiene; nitrites such as benzonitrile, and acetonitrile; and acetylacetone.

The amount of the ligand is usually between 0.1 and 10,000 mol %, preferably between 10 and 5,000 mol % based on the catalyst of the metal of group VIII in the periodic table.

The reaction temperature is usually between room temperature and 500° C., preferably between 50 and 300° C.

The reaction time varies depending on the reactivity of the triazine derivatives of formula (I). It is, normally, between 1 and 100 hours, preferably between 2 and 50 hours. Although the reaction proceeds in the absence of a solvent, a solvent can be used as required in view of operability and the like.

The solvent is not particularly limited so long as it is inert to the reaction. Examples of the solvent include ethers such as tetrahydrofuran, diethyl ether, diethylene glycol diethyl ether, and 1,4-dioxane; alcohols such as methanol, ethanol, 1-propanol, 2-propanol, 1-butanol, 2-butanol, iso-butanol, 2-methyl-2-propanol, cyclohexanol and benzyl alcohol; aromatic hydrocarbons such as benzene, toluene, xylene, mesitylene, cumene, chlorobenzene, o-dichlorobenzene, m-dichlorobenzene, p-dichlorobenzene and, tetrahydronaphthalene; aliphatic hydrocarbons such as: n-hexane, cyclohexane, n-octane, and n-decane; esters such as methyl acetate, ethyl acetate, butyl acetate, ethyl propionate, methyl benzoate and ethyl benzoate; amides such as N,N-dimethylformamide, N,N-dimethylacetamide and N-methylpyrrolidone; ureas such as 1,3-dimethylimidazolidinone, and N,N,N',N'-tetramethylurea; and water. They may be used in either single or in combination. Excess amount of aldehyde and ketone derivatives of the formula (II) may be used as a solvent.

The reaction of the present invention is carried out under an atmosphere of pure hydrogen gas or hydrogen-containing gas. The pressure of gases is between 0.1 to 500 kg/cm², preferably, between 0.5 to 200 kg/cm² which gives good results. In a case of hydrogen-containing gas, as a dilution gas, various gases which do not directly participate the reaction. For example, nitrogen, argon and helium are ordinarily used. Carbon dioxide and air are also available. For stabilizing the product and the catalyst, ammonia and carbon monoxide are also used. In a case of using these mixed gases, there is no problem when there is hydrogen-partial pressure required for the reaction. As the total pressure, it is desirable to be reacted within the pressure range of between 0.5 to 500 kg/cm², preferably, between 1.0 to 300 kg/cm².

After the completion of the reaction, unreacted triazines are removed through filtration or the like, and the solvent is then removed through distillation or the like as required, or a product is extracted as a two-phase system of water and an organic solvent, and is then purified and isolated through recrystallization, distillation, separation using chromatography or the like. The metal-complex catalysts are collected by filtration or the like in a case of solid or elements-carried catalysts. The organic metal complex catalyst is collected by the residue obtained after collecting the product through distillation, recrystallization or the like and removing the solvent. The catalyst with water-soluble ligand is collected in an aqueous layer as a water-soluble metal complex through extraction. Thus, the catalysts can be separated, collected and reused in various forms.

The substituted-1,3,5-triazine derivatives obtained by the method for alkylation of amino groups on carbon atoms of the 1,3,5-triazine ring in the present invention are 1,3,5-triazine derivatives of the formula (III)

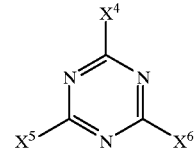

(III)

[wherein at least one of $X^4$, $X^5$ and $X^6$ independently represents $NR^6R^7$ {in which $R^6$ and $R^7$ independently represent a hydrogen atom (provided that a case where $R^6$ and $R^7$ of $X^4$, $X^5$ and $X^6$ are all hydrogen atoms is excluded), a $C_{1\text{-}20}$ alkyl group (said alkyl group is optionally substituted with a halogen atom, a trifluoromethyl group, a hydroxyl group, a $C_{1\text{-}6}$ alkoxy group, a $C_{1\text{-}6}$ haloalkoxy group, an aryloxy group, a $C_{2\text{-}7}$ alkoxycarbonyl group, a $C_{2\text{-}7}$ acyloxy group, an amino group, a $C_{1\text{-}8}$ monoalkylamino group, a $C_{2\text{-}12}$ dialkylamino group or a phenyl group (said phenyl group is optionally substituted with a halogen atom, a $C_{1\text{-}6}$ alkyl group, a hydroxyl group or a $C_{1\text{-}6}$ alkoxy group)), or a $C_{2\text{-}20}$ alkenyl group (said alkenyl group is optionally substituted with a halogen atom, a trifluoromethyl group, a hydroxyl group, a $C_{1\text{-}6}$ alkoxy group, a $C_{1\text{-}6}$ haloalkoxy group, an aryloxy group, a $C_{2\text{-}7}$ alkoxycarbonyl group, a $C_{2\text{-}7}$ acyloxy group, an amino group, a $C_{1\text{-}8}$ monoalkylamino group, a $C_{2\text{-}12}$ dialkylamino group or a phenyl group (said phenyl group is optionally substituted with a halogen atom, a $C_{1\text{-}6}$ alkyl group, a hydroxyl group or a $C_{1\text{-}6}$ alkoxy group)) or $R^6$ and $R^7$ may together form —$(CH_2)_{2\text{-}5}$—, —$CH_2CH_2$—$(C_{1\text{-}8}$ alkyl)N—$CH_2CH_2$— or —$CH_2CH_2$—O—$CH_2CH_2$— in which an alkylene chain is optionally substituted with one or two $C_{1\text{-}8}$ alkyl groups}, and $X^4$, $X^5$ and $X^6$ which are not $NR^8R^7$ independently represent a $C_{1\text{-}20}$ alkyl group {said alkyl group is optionally substituted with a halogen atom, a hydroxyl group, a $C_{1\text{-}6}$ alkoxy group, a carboxyl group, a $C_{2\text{-}7}$ alkoxycarbonyl group, a $C_{2\text{-}10}$ acyloxy, an amino group, a $C_{1\text{-}8}$ monoalkylamino group, a $C_{2\text{-}12}$ dialkylamino group or an aryl group (said aryl group is optionally substituted with a halogen atom, a $C_{1\text{-}6}$ alkyl group, a hydroxyl group or a $C_{1\text{-}6}$ alkoxy group)}, a $C_{2\text{-}20}$ alkenyl group {said alkenyl group is optionally substituted with a halogen atom, a hydroxyl group, a $C_{1\text{-}6}$ alkoxy group, a carboxyl group, a $C_{2\text{-}7}$ alkoxycarbonyl group, a $C_{2\text{-}10}$ acyloxy group, an amino group, a $C_{1\text{-}8}$ monoalkylamino group, a $C_{2\text{-}12}$ dialkylamino group or an aryl group (said aryl group is optionally substituted with a halogen atom, a $C_{1\text{-}6}$ alkyl group, a hydroxyl group or a $C_{1\text{-}6}$ alkoxy group)}, a phenyl group {said phenyl group is optionally substituted with a $C_{1\text{-}6}$ alkyl group, a halogen atom, a hydroxyl group, a $C_{1-6}$ alkoxy group, an aryloxy group, a $C_{2-10}$ acyloxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}, a halogen atom, a $C_{1-10}$ alkoxy group {said alkoxy group is optionally substituted with a halogen atom, a hydroxyl group, a $C_{1-6}$ alkoxy group, an aryloxy group, a carboxyl group, a $C_{2-7}$ alkoxycarbonyl group, a $C_{2-10}$ acyloxy group, an amino group, a $C_{1-8}$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}, or a $C_{1-10}$ alkylthio group {said alkylthio group is optionally substituted with a halogen atom, a hydroxyl group, a $C_{1-6}$ alkoxy group, an aryloxy group, a carboxyl group, a $C_{2-7}$ alkoxycarbonyl group, a $C_{2-10}$ acyloxy group, an amino group, a $Cl_8$ monoalkylamino group, a $C_{2-12}$ dialkylamino group or an aryl group (said aryl group is optionally substituted with a halogen atom, a $C_{1-6}$ alkyl group, a hydroxyl group or a $C_{1-6}$ alkoxy group)}].

Preferable are substituted-1,3,5-triazine derivatives of the formula (III) are substituted 1,3,5-trizaine derivatives in which $R^6$ and $R^7$ of $NR^6R^7$ of $X^4$, $X^5$ and $X^6$ independently represent a hydrogen atom (provided that a case in; where $R^6$ and $R^7$ of $X^4$, $X^5$ and $X^6$ are all hydrogen atoms is excluded), a $C_{1-20}$ alkyl group (said alkyl group is optionally substituted with a halogen atom, a hydroxyl group, a $C_{1-6}$ alkoxy group or a phenyl group (said phenyl group is optionally substituted with a halogen atom, a $C_{1-6}$ alkyl group, a hydroxyl group or a $C_{1-6}$ alkoxy group)}, or a $C_{2-20}$ alkenyl group (said alkenyl group is optionally substituted with a halogen atom, a hydroxyl group, a $C_{1-6}$ alkoxy group, a phenyl group (said phenyl group is optionally substituted with a halogen atom, a $C_{1-6}$ alkyl group, a hydroxyl group or a $C_{1-6}$ alkoxy group)}, or $R^6$ and $R^7$ may together form $-(CH_2)_{3-5}-$, $-CH_2CH_2-(C_{1-8}$ alkyl$)N-CH_2CH_2-$ or $-CH_2CH_2-O-CH_2CH_2-$ in which an alkylene chain is optionally substituted with one or two $C_{1-8}$ alkyl groups, and $X^4$, $X^5$ and $X^6$ which are not $NR^4R^5$ independently represent a $C_{1-20}$ alkyl group {said alkyl group is optionally substituted with a halogen atom, a hydroxyl group, a $C_{1-6}$ alkoxy group or an aryl group (said aryl group is optionally substituted with a halogen atom, a $C_{1-6}$ alkyl group, a hydroxyl group or a $C_{1-6}$ alkoxy group)}, a phenyl group (said phenyl group is optionally substituted with a $C_{1-6}$ alkyl group, a halogen atom, a hydroxyl group or a $C_{1-6}$ alkoxy group), a halogen atom or a $C_{1-10}$ alkoxy group {said alkoxy group is optionally substituted with a halogen atom, a hydroxyl group, a $C_{1-6}$ alkoxy group or an aryl group (said aryl group is optionally substituted with a halogen atom, a $C_{1-6}$ alkyl group, a hydroxyl group or a $C_{1-6}$ alkoxy group)}.

More preferable substituted-1,3,5-triazine derivatives of the formula (III) are substituted 1,3,5-triazine derivatives of the formula (III) wherein $R^6$ and $R^7$ of $NR^6R^7$ independently represents a hydrogen atom (provided that a case where $R^6$ and $R^7$ of $X^4$, $X^5$ and $X^6$ are all hydrogen atoms is excluded) or a $C_{1-20}$ alkyl group (said alkyl group is optionally substituted with a hydroxyl group, a $C_{1-6}$ alkoxy group or a phenyl group), or $R^6$ and $R^7$ may together form $-(CH_2)_{4-5}-$, $-CH_2CH_2-(C_{1-8}$ alkyl$)N-CH_2CH_2-$ or $-CH_2CH_2-O-CH_2CH-$ in which an alkylene chain is desirably substituted with one or two $C_{1-8}$ alkyl groups, and $X^4$, $X^5$ and $X^6$ which are not $NR^4R^5$ independently represent a $C_{1-20}$ alkyl group, a phenyl group or a $C_{1-10}$ alkoxy group.

As stated above, various compounds are usable as starting 1,3,5-triazine derivatives and aldehydes and ketones in the process of the present invention. The 1,3,5-triazine derivatives having various substituents can be obtained from combinations of starting 1,3,5-triazine derivatives and aldehydes and ketones by the method of the present invention.

As mentioned above, typical starting materials of the present invention are 1,3,5-triazine derivatives, such as melamine, melamine derivatives and guanamine derivatives, as well as aldehydes and ketones such as those derived from petrochemicals. Typical products are obtained by the combinations of these starting materials. Further, for example, substituted melamine derivatives obtained by alkylation of melamine by the present invention can be used as starting 1,3,5-triazine derivatives of the present invention if a partial —NH— is present on a carbon atom of their triazine rings.

The starting materials which can be applied to the reaction of the present invention are not limited by the costs of the starting materials and ease of obtainment thereof. However, the range of the reaction in the present invention is more clarified by illustrating specific examples of the substituents of the starting materials and the products.

Specific examples of $NHR^1$, $NR^2R^3$ and $NR^6R^7$ among the substituents indicated by $X^1$, $X^2$ and $X^3$ of formula (I) representing the starting materials and by $X^4$, $X^5$ and $X^6$ of formula (III) representing the products include amino, methylamino, ethylamino, isopropylamino, n-butylamino, i-butylamino, sec-butylamino, tert-butylamino, cyclohexylamino, cyclohexylmethylamino, n-octylamino, n-decylamino, n-hexadecylamino, dimethylamino, diethylamino, diisopropylamino, di-n-butylamino, di-i-butylamino, di-sec-butylamino, methyl-tert-butylamino, methylcyclohexylamino, cyclohexylmethylamino, di-n-octylamino, dicyclohexylmethylamino, chloroethylamino, 3-chloropropylamino, hydroxyethylamino, 4-hydroxybutylamino, 5-hydroxypentylamino, bis(hydroxylethyl)amino, trifluoroethylamino, 2-trifluoropropylamino, 2-ethoxyethylamino, 3-methoxypropylamino, 2-pentyloxyethylamino, 3-cyclohexyloxypropylamino, 2-chloroethoxyethylamino, 5-monofluoropentyloxypentylamino, 2-methoxycarbonylethylamino, 2-ethoxycarbonylethylamino, tert-butoxycarbonylethylamino, 2-cyclohexyloxycarbonylethylamino, acetoxymethylamino, 3-acetoxypropylmethylamino, cyclohexanoyloxyethylamino, 2-benzoyloxypropylamino, 2-aminoethylamino, 6-aminohexylamino, cyclohexylaminoethylamino, dimethylaminoethylamino, diethylaminoethylamino, methylphenylamino, benzylamino, dibenzylamino, N-benzyl-N'-methylamino, 2-phenylethylamino, 3-(4-chlorophenyl)-propylamino, 2-(4-cyclohexylphenyl)ethylamino, 2-(3-fluorophenyl)-pentylamino, 4-methoxybenzylamino, 2-chloro-4-fluorobenzylamino, 3,5-dimethylbenzylamino, 4-cyclopentyloxybenzylamino, 2-(2-chloro-4-fluoro-5-isopropylphenyl)-propylamino, 4-hydroxybenzylamino, 4-hydroxyphenylethylamino, allylamino, methallylamino, 3-cyclopentenylamino, 3-cyclohexenylamino, 3-(6-trifluoromethyl)-cyclohexenylamino, diallylamino, dimethallylamino, 3-(l-methoxy)-allyl, crotylamino, chloromethoxyethylamino, ethoxycarbonylallylamino, cinnamylamino, 4-chlorocinnamylamino, N-(4-methylcinnamyl)-N'-methylamino and 4-methoxycinnamylamino groups.

Specific examples of the group formed by binding of $R^2$ and $R^3$ of $NR^2R^3$ or by binding of $R^6$ and $R^7$ of $NR^3R^7$ include aziridino, pyrrolidino, piperidino, N-methylpiperazino and morpholino groups.

Specific examples of the optionally substituted $C_{1-20}$ alkyl groups include methyl, ethyl, n-propyl, n-butyl, i-butyl, sec-butyl, n-amyl, i-amyl, hexyl, cyclohexyl, cyclohexylmethyl, heptyl-, octyl, 2-ethylhexyl, nonyl, decyl, hexadecyl, octadecyl, trifluoromethyl, 3-chloropropyl, 2-trifluoromethylethyl, hydroxymethyl, 2-hydroxyethyl, methox-methyl, methoxyethyl, ethoxymethyl, cyclohexylmethoxyethyl, 2-carboxyethyl, 3-carboxypropyl, methoxycarbonylmethyl, methoxycarbonylethyl, tert-butoxycarbonylmethyl, cyclohexyloxycarbonylethyl, 2-propanoylethyl, benzoylmethyl, 2,4,6-trimethylphenylbenzoylmethyl, acetyloxymethyl, benzoyloxymethyl, 3-(tert-butylcarbonyloxy)-propyl, 3-aminopropyl, cyclohexylaminomethyl, 2-cyclopentylaminoethyl, dimethylaminomethyl, diethylaminomethyl, diisopropylaminomethyl, di-n-butylaminomethyl, di-i-butylaminomethyl, di-sec-butylaminomethyl, methyl-tert-butylaminomethyl, methylcyclohexylaminomethyl, cyclohexylmethylaminomethyl, benzyl, 4-methylbenzyl, 4-methoxybenzyl, 2-chloro-4-fluorobenzyl, 3,5-dimethylbenzyl and 4-cyclopentyloxybenzyl groups.

Specific examples of the optionally substituted $C_{2-20}$ alkenyl groups include vinyl, isopropenyl, 1-butenyl, 3-hexenyl, allyl, methallyl, crotyl, 2-chloroallyl, methoxyvinyl, ethoxyvinyl, cyclohexylvinyl, 4-phenyl-2-butenyl, 2-carboxylvinyl, ethoxycarbonylvinyl, tert-butoxycarbonylvinyl, acetylvinyl, acetylallyl, 3-benzoylallyl, acetyloxyvinyl, cyclohexanoyloxyvinyl, dimethylaminovinyl, 4-diethylaminobutenyl, dicyclohexylaminovinyl, cinnamyl, 4-chlorocinnamyl, 3,5-dimethoxycinnamyl, 2,4,6-trimethylcinnamyl, styryl, 2,4-dichlorostyryl, 6-dodecen-1-yl and 1,2-diphenylvinyl groups.

Specific examples of the optionally substituted phenyl group include phenyl, p-toluyl, m-toluyl, o-toluyl, 3,5-dimethylphenyl, 4-cyclohexylphenyl, 2,4,6-trimethylphenyl, 2-methyl-4-isopropylphenyl, 2-chlorophenyl, 2,4-dichlorophenyl, 2-fluoro-4-chlorophenyl, 3,5-dimethoxyphenyl, 4-cyclopentyloxyphenyl, m-phenoxyphenyl, 4-(2-naphthyloxy)phenyl, 3-acetoxyphenyl group, 3-benzoyloxyphenyl, 4-carboxyphenyl, 4-methoxycarbonylphenyl, 3-cyclohexyloxycarbonylphenyl, 2-acetylphenyl, 4-octanoylphenyl, 4-acetyloxyphenyl, 3-cyclohexylcarbonyloxyphenyl, 2-dimethylaminophenyl, 4-diethylaminophenyl, 4-diisopropylaminophenyl, 3-di-n-butylaminophenyl, 3-di-i-butylaminophenyl, 2-di-sec-butylaminophenyl, 4-methyl-tert-butylaminophenyl, 4-methylcyclohexylaminophenyl, 4-cyclohexyl-methylaminophenyl, 4-biphenyl, 4-(2-naphthyl)-phenyl, 4-(4-chlorophenyl)-phenyl and 4-(5-(1-methyl-3-chloropyrazolo)-yl)-phenyl groups.

Specific examples of the halogen atom include fluorine, chlorine, bromine and iodine atoms.

Specific examples of the optionally substituted a $C_{1-10}$ alkoxy group include methoxy, ethoxy, n-propyloxy, i-propyloxy, n-butyloxy, i-butyloxy, sec-butyloxy, tert-butyloxy, n-amyloxy, i-amyloxy, hexyloxy, cyclohexyloxy, cyclohexylmethyloxy, pentyloxy, octyloxy, 2-ethylhexyloxy, nonyloxy, decyloxy, hexadecyloxy, octadecyloxy, trifluoromethyloxy, 3-cyloropropyloxy, 2-trifluoromethylethyloxy, methoxymethoxy, methoxyethoxy, ethoxymethoxy, cyclohexylmethoxyethoxy, 2-carboxyethoxy, 3-carboxypropoxy, methoxycarbonylmethoxy, methoxycarbonylethoxy, tert-butoxycarbonylmethoxy, cyclohexyloxycarbonylethoxy, 2-propanoylethoxy, benzoylmethoxy, 2,4,6-trimethylphenylbenzoylmethyloxy, acetyloxymethyloxy, benzoyloxymethyloxy, 3-(tert-butylcarbonyloxy)-propyloxy, dimethylaminomethyloxy, diethylaminomethyloxy, diisopropylaminomethyloxy, di-n-butylaminomethyloxy, di-i-butylaminomethyloxy, di-sec-butylaminomethyloxy, methyl-tert-butylaminomethyloxy, methylcyclohexylaminomethyloxy, cyclohexylmethylaminomethyloxy, benzyloxy, 4-methylbenzyloxy, 4-methoxybenzyloxy, 2-chloro-4-fluorobenzyloxy, 3,5-dimethylbenzyloxy and 4-cyclopentyloxybenzyloxy groups.

Specific examples of the optionally substituted $C_{1-10}$ alkylthio group include methylthio, ethylthio, n-propylthio, i-propylthio, n-butylthio, i-butylthio, sec-butylthio, tert-butylthio, n-amylthio, i-amylthio, hexylthio, cyclohexylthio, cyclohexylmethylthio, pentylthio, octylthio, 2-ethylhexylthio, nonylthio, decylthio, hexadecylthio, octadecylthio, trifluoromethylthio, 3-chloropropylthio, 2-trifluoromethylethylthio, methoxymethylthio, methoxyethylthio, ethoxymethylthio, cyclohexylmethoxyethylthio, 2-carboxyethylthio, 3-carboxypropylthio, methoxycarbonylmethylthio, methoxycarbonylethylthio, tert-butoxycarbonylmethylthio, cyclohexyloxycarbonylethylthio, 2-propanoylethylthio, benzoylmethylthio, 2,4,6-trimethylphenylbenzoylinethylthio, acetyloxymethylthio, benzoyloxymethylthio, 3-(tert-butylcarbonyloxy)-propylthio, dimethylaminomethylthio, diethylaminomethylthio, diisopropylaminomethylthio, di-n-butylaminomethylthio, di-i-butylaminomethylthio, di-sec-butylaminomethylthio, methyl-tert-butylaminomethylthio, methylcyclohexylaminomethylthio, cyclohexylmethylaminomethylthio, benzylthio, 4-methylbenzylthio, 4-methoxybenzylthio, 2-chloro-4-fluorobenzylthio, 3,5-dimethylbenzylthio and 4-cyclopentyloxybenzylthio groups.

The aldehydes and ketones which are subjected to the reaction of the present invention as another starting material can be commercially available aldehydes and ketones. Specific examples of the substituent indicated by $R^4$ and $R^5$ include hydrogen atom, methyl, ethyl, n-propyl, n-butyl, i-butyl, sec-butyl, n-amyl, i-amyl, hexyl, cyclohexyl, cyclohexylmethyl, heptyl, octyl, 2-ethylhexyl, nonyl, decyl, hexadecyl, octadecyl, trifluoromethyl, 3-chloropropyl, 2-trifluoromethylethyl, hydroxyethyl, methoxymethyl, methoxyethyl, ethoxymethyl, cyclohexylmethoxyethyl, 2-carboxyethyl, 3-carboxypropyl, methoxycarbonylmethyl, methoxycarbonylethyl, tert-butoxycarbonylmethyl, cyclohexyloxycarbonylethyl, 2-propanoylethyl, benzoylmethyl, 2,4,6-trimethylphenylbenzoylmethyl acetyloxymethyl, benzoyloxymethyl, 3-(tert-butylcarbonyloxy)-propyl, dimethylaminomethyl, diethylaminomethyl, diisopropylaminomethyl, di-n-butylaminomethyl, di-i-butylaminomethyl, di-sec-butylaminomethyl, methyl-tert-butylaminomethyl, methylcyclohexylaminomethyl, cyclohexylmethylaminomethyl, benzyl, 4-methylbenzyl; 4-methoxybenzyl, 2-chloro-4-fluorobenzyl, 3,5-dimethylbenzyl, 4-cyclopentyloxybenzyl, allyl, homoallyl, methallyl, 3-cyclopentenyl, 3-cyclohexenyl, 3-(6-trifluoromethyl)-cyclohexenyl, 3-(1-methoxy)-allyl, crotylamino, cinnamyl, 4-methylcinnamyl, 4-chlorocinnamyl, 4-ethoxycinnamyl and 2,4,6-trimethylcinnamyl groups As examples that $R^4$ and $R^5$ together form alkylene group —$(CH_2)_{3-5}$—, trimethylene, tetramethylene and pentamethylene are raised.

These examples of the substituents are typical ones, and the substituents of the present invention are not limited thereto.

Any amount of aldehyde or ketone derivatives containing the above-mentioned substituents is possible according to various uses. It is generally effective in the range between 0.01 to 500 times in mol. based on the starting 1,3,5-triazine derivative compound, preferably, between 0.1 to 50 times in mol. from the viewpoints of reaction and operation. In the treatment after the completion of the reaction, unreacted triazines are crystallized and removed by filtration or the like, after which the solvent is removed by distillation or the like as required. Or the product is extracted as a two-phase system of water and an organic solvent, and the reaction product is then purified and isolated by recrystallization, distillation, separation using chromatography or the like.

In a case of the element-carried catalysts, when a fixed bed is used, the bed can be used continuously as it is and when a suspension bed (liquid-phase reaction) is used, easy separation can be possible through filtration and the like. In a case of the organic metal complex catalyst, the catalyst can be collected from residues obtained by removing solvents and products through distillation, recrystallization or the like. In a case that the catalysts is made to be water-soluble by using ligand and the like, the water-soluble ligand can be collected in an aqueous layer through aqueous extraction. As mentioned above, it is possible to separate and collect catalysts from the product systems in various forms and therefore, a so-called "recycle-process" which is sufficiently used in industrial scale can be established.

BEST MODE OF CARRYING OUT THE INVENTION

The present invention will be illustrated more specifically by referring to the following Examples. However, the present invention is not limited thereto.

In all of the Examples, products were already and separately produced as specimens according to the processes described in "J. Am. Chem. Soc., vol. 73, p. 2984 (1951)" or in Japanese Patent Application Laid-open No. He 3-215564. Referential examples show synthesis examples using cyanuric chloride. The calibration curve was made by isolated products as pure derivatives and internal standard substances. Each product amount in reaction products is accurately obtained under the following conditions by using high-performance liquid chromatography. All of the yields shown in the Examples were described on the standard of the starting triazine compounds.

The conditions for analysis of high-performance liquid chromatography (HPLC) are as follows.

Method of determining an amount of starting triazine such as melamines:
Eluent: $CH_3CN/H_2O=1/1$ (v/v)
Detection method: UV 240 nm
Column: Inertsil Ph manufactured by GL Science, 150 mm×4.6 mm φ
Flow rate: 1.0 ml/min
Analysis temperature: 40° C.
Internal standard substance: di-n-butyl phthalate
(Method of determining amounts of a product and a part of a starting material (a part of alkylaminotriazines)):

Eluent: $CH_3CN/H_2O$ = 40/60 (v/v),
↓ 15 minutes later,
$CH_3CN/H_2O$ = 1/1 (v/v),
↓ retained for 15 minutes
(gradient analysis)

Detection method: UV 230 nm
Column: Inertsil $C_8$ manufactured by GL Science, 150 mm×4.6 mm φ
Flow rate: 1.0 ml/min
Temperature: 35° C.
Internal standard substance: di(2-ethylhexyl)phthalate ester

REFERENTIAL EXAMPLE 1

(Production of 4,6-diamino-2-n-butylamino-1,3,5-triazine)

184.5 g (1.0 mol.) of cyanuric chloride were dissolved in 800 mL of acetonitrile at room temperature. Then, the solution was cooled to 0° C. The cooled solution was dropwise added with 303.7 g (5.0 mol.) of an aqueous 28-% ammonium solution over two hours while vigorously stirring in such a manner that the reaction temperature was kept less than 10° C. After the completion of the dropwise addition, the cooling was stopped and the mixture was stirred at room temperature for one hour. The mixture was gradually warmed and the mixture was further reacted at 45° C. for four hours. After cooling, the obtained product was separated through filtration and then, washed with a large amount of water. The filtered products were dried at 50° C. for six hours under vacuum to obtain 115 g of 2,4-diamino-6-chloro-1,3,5-triazine (yield: 79%).

A mixture solution of 14.5 g (0.1 mol.) of the obtained 2,4-diamino-6-chloro-1,3,5-triazine, 100 mL of water and 29.2 g (0.4 mol.) of butylamine was warmed while stirring and finally, reacted at reflux temperature for six hours. After the completion of the cooling of the reaction liquid, an obtained product was separated through filtration and, further washed fully with a large amount of water and successively washed with toluene. The filtered product was dried at 70° C. for six hours under vacuum to obtain 17.5 g of 4,6-diamino-2-n-butylamino-1,3,5-tirazine (yield: 96%).

melting point: 167° C.

REFERENTIAL EXAMPLE 2

(Production of 2-amino-4,6-bis(n-butylamino)-1,3,5-triazine)

18.5 g (0.1 mol.) of cyanuric chloride was dissolved in 150 mL of acetonitrile. The solution was cooled to 0° C. and the cooled solution was dropwise added, while stirring, with a solution of 7.3 g (0.1 mol.) of butylamine in 20 mL of water over one hour in such a manner that the reaction temperature did not raise over 5° C. While further continuing the stirring, a solution of 10.0 g (0.1 mol.) of potassium hydrogencarbonate in 100 mL of water was dropwise added to the mixture at the same temperature and stirred for three hours. After the completion of the conversion of the resulting product into 2-butylamino-4,6-dichloro-1,3,5-tirazine was recognized by a high-performance liquid chromatography, 24.3 g (0.4 mol.) of an aqueous 28-% ammonium solution were added. The temperature was raised to 50° C. and the reaction was carried out for five hours. After the cooling, an obtained product was separated through filtration and washed fully with a large amount of water. An obtained crude product was suspended in 100 mL of water and added with 29.2 g (0.4 mol.) of butylamine and reacted for six hours under heating and refluxing. After the completion of the cooling, the resulting product was added with 200 mL of toluene and vigorously stirred and then, the aqueous layer was separated. Further, after the toluene layer was thrice washed with each 150 mL of water, toluene was distilled off from the organic layer under heating and reduced pressure to obtain 22.1 g of 2-amino-4,6-bis-(n-butylamino)-1,3,5-triazine (yield: 93%).

melting point: 73° C.

REFERENTIAL EXAMPLE 3
(Production of 2,4,6-tris(n-butylamino)-1,3,5-triazine)

18.5 g (0.1 mol.) of cyanuric chloride were dissolved in 150 mL of acetonitrile. The mixture solution was cooled to 0° C. The cooled solution was dropwise added with a solution of 14.6 g (0.2 mol.) of butylamine in 20 mL of water over one hour while stirring in such a manner that the temperature did not raise over 5° C. While further continuing the stirring, a solution of 20.0 g (0.2 mol.) of potassium hydrogenecarbonate in 100 mL of water was dropwise added to the solution at the same temperature. Thereafter, the reaction temperature was gradually raised and the stirring was continued at 45° C. for eight hours. After the completion of the conversion of the resulting product into 2,4-bis (butylamino)-6-chloro-1,3,5-triazine was recognized by a high-performance liquid chromatography, the obtained produt was cooled and separated through filtration. After the filtrated cake was fully wahsed with a large amount of water, the obtained 2,4-bis(butylamino)-6-chloro-1,3,5-triazine was suspended in 100 mL of water and added with 29.2 g (0.4 mol.) of butylamine and further reacted for six hours under heat-reflux. After cooling, the resulting product was added with 200 mL of toluene and vigorously stirred. Thereafter, the aqueous layer was separated. After the toluene layer was further washed thrice with each 150 mL of water, toluene was distilled off from the organic layer under heating and reduced pressure to obtain 28.2 g of 2,4,6-tris (n-butylamino)-1,3,5-triazine (yield: 96%).

(property: oil)

REFERENTIAL EXAMPLE 4
(Production of 4,6-diamino-2-cyclohexylamino)-1,3,5-triazine)

A mixture of 14.5 g (0.1 mol.) of 2,4-diamino-6-chloro-1,3,5-triazine produced in the Referential Example 1 and 280 mL of water was heated to 85° C. and was dropwise added with 29.7 g (0.3 mol.) of cyclohexylamine over two hours and further reacted at the same temperature for one hour. Successively, a solution of 6.0 g of sodium hydroxide in 30 mL of water was dropwise added to the reaction solution over one hour and the reaction was further continued for one hour. 200 mL of toluene was added in the reaction solution and( stirred at 85° C. for one hour. The stirring was continued to cool the termperature of the solution to the room temperature. Product was separated from the reaction solution through filtration and washed twice with each 100 mL of toluene and twice with each 100 mL of water, successively. The filtrated product was dried at 70° C. for six hours under vacuum to obtain 17.5 g of 4,6-diamino-2-cyclohexylamino-1,3,5-triazine (yield: 84%).

melting point: 151° C.

REFERENTIAL EXAMPLE 5
(Production of 2-amino-4,6-bis(cyclohexylamino)-1,3,5-triazine)

18.5 g (0.1 mol.) of cyanuric chloride were dissolved in 500 mL of acetonitrile and the solution was cooled to 0° C. While stirring, a solution of 9.9 g (0.1 mol.) of cyclohexyamine, 10.5 g (0.104 mol.) of triethylamine and 330 mL of water was dropwise added to the resulting solution over three hours in such a manner that the reaction temperature did not raise over 5° C. After the stirring was further continued at the same temperature for two hours, 683 mL of an aqueous 28-% ammonium solution of were dropwise added, and stirred at 5° C. for one hour, at 20° C. for one hour and at 50° C. for one hour. Successively, 55.5 g (0.56 mol.) of cyclohexyamine was added to the resulting solution at the reaction temperature of less than 60° C. and reacted at 70° C. for four hours. Further, 1600 mL of water was dropwise added to the reaction solution, while keeping the temperature at 70° C. and successively, gradually cooled to 10° C. After cooling, product was separated through filtration and washed five times with each 660 mL of water. Filtrated product was dried at 70° C. for six hours under vacuum to obtain 16.4 g of 2-amino-4,6-bis (cyclohexylamino)-1,3,-5-triazine (yield: 56%).

melting point: 153° C.

REFERENTIAL EXAMPLE 6
(Production of 2,4,6-tris(cyclohexylamino)-1,3,5-triazine)

18.5 g (0.1 mol.) of cyanuric chloride were dissolved in 400 mL of 1,4-dioxane. The mixture solution was warmed to 50° C. While stirring, the warmed solution was dropwise added with 60.2 g (0.6 mol.) of cyclohexylamine over two hours in such a manner that the reaction temperature did not raise over 50° C. While continuing further stirring, the temperature was raised to 85° C. and 60.2 g (0.61 mol.) of cyclohexylamine by keeping the temperature. Thereafter, the temperature was again raised and the reaction was carried out at the reaction temperature of 95° C. for six hours. 230 g of water were added to the reaction solution so that the temperature did not fall less than 90° C. and then, cooled. to the room temperature while stirring. Product was separated, from the reaction solution through filtration and washed with each 150 mL of water four times. The filtered product was dried at 70° C. for six hours under vacuum to obtain 34.2 g of 2,4,6-tris(cyclohexylamino)-1,3,5-triazine (yield: 225° C.)

Example 1

A 100-mL stainless steel autoclave was charged with 2.52 g (20.0 mmol.) of melamine, 52.0 mg (0.2 mmol.) of ruthenium trichloride hydrate, 364.0 mg (1 mmol) of sodium diphenylphosphinobenzene-3-sulfonate, 8.64 g (0.12 mol.) of butyraldehyde and 30 mL of diethylene glycol dimethyl ether. After the inside of the system was fully purged with a nitrogen gas, the reaction was conducted at a reaction temperature of 200° C. for ten hours and under a synthesized gas ($H_2/CO=1/1$)(initial pressure of 100 kg/cm$^2$). After the completion of the reaction, unreacted melamine was determined. As a result, the conversion ratio of the starting materials were 48%. As a result of analyzing the reaction products, respective products were obtained in the following yields:

2-n-butylamino-4,6-diamino-1,3,5-triazine at 6.0%,
2,4-bis(n-butylamino)-6-amino-1,3,5-triazine at 7.7%,
2,4,6-tris(n-butylamino)-1,3,5-triazine at 23.3%, and
2-di-n-butylamino-4,6-bis(n-butylamino)-1,3,5-triazine at 5.3%.

Example 2

A 100-mL stainless steel autoclave was charged with 2.52 g (20.0 mmol.) of melamine, 63.9 mg (0.1 mmol.) of triruthenium dodecacarbonyl, 4.32 g (60.0 mmol.) of butyraldehyde and 30 mL of diethylene glycol dibutyl ether. After the inside of the system was fully purged with a nitrogen gas, the reaction was conducted at a reaction temperature of 200° C. for ten hours and under a synthesized gas ($H_2/CO=1/1$)(initial pressure of 100 kg/cm$^2$. After the completion of the reaction, unreacted melamine was determined. As a result, the conversion ratio of the starting material was 95%. The solvent was distilled off from the reaction solution and added with 100 mL of toluene and dissolved to separate unreacted melamine through filtration. As a result that the reaction products were analyzed, the following were produced at the respective yields:

2-n-butylamino-4,6-diamino-1,3,5-triazine at 12.5%, 2,4-bis(n-butylamino)-6-amino-1,3,5-triazine at 14.4%, 2,4,6-tris(n-butylamino)-1,3,5-triazine at 52.1%, 2-di-n-butylamino-4,6-bis(n-butylamino)-1,3,5-triazine at 8.6%, and 2,4-bis(di-n-butylamino)-6-n-butylamino-1,3,5-triazine at 3.2%.

Example 3

A 100-mL stainless steel autoclave was charged with 2.52 g (20.0 mmol.) of melamine, 92.5 mg (0.1 mmol.) of chlorotris(triphenylphosphine)rhodium, 4.32 g (60.0 mmol.) of butyraldehyde and 30 mL of diethylene glycol dibutyl ether. After the inside of the system was fully purged with an argon gas, the reaction was conducted at a reaction temperature of 250° C. for one hour and under a synthesized gas ($H_2/CO=1/1$) (initial pressure of 100 kg/cm$^2$). After the completion of the reaction, unreacted melamine was determined. As a result, the conversion ratio of the starting materials was 28%. This solvent was distilled off from the reaction solution and added with 100 mL of toluene and dissolved to separate unreacted melamine through filtration. Toluene was distilled off from the toluene solution and concentrated to make the total amount to be 10 mL for the crystallization. Produced crystals were collected through filtration to obtain 0.71 g of 2-n-butylamino-4,6-diamino-1,3,5-tirazine (yield: 19.5%).

Example 4

A 100-mL stainless steel autoclave was charged with 2.52 g (20.0 mmol.) of melamine, 63.9 mg (0.1 mmol.) of triruthenium dodecacarbonyl, 6.36 g (60.0 mmol.) of benzaldehyde and 30 mL of 1,4-dioxane. After the inside of the system was fully purged with a nitrogen gas, the reaction was conducted at a reaction temperature of 200° C. for ten hours and under a synthesized gas ($H_2/CO=1/1$)(initial pressure of 100 kg/cm$^2$). After the completion of the reaction, unreacted melamine was determined. As a result, the conversion ratio of the starting materials was 98%. The solvent was distilled off from the reaction solution and added with 100 mL of toluene and dissolved to separate unreacted melamine through filtration. As a result that the reaction products were analyzed, the following were produced at the respective yields:

2-benzylamino-4,6-diamino-1,3,5-triazine at 10.4%, 2,4-bis(benzylamino)-6-amino-1,3,5-triazine at 12.0%, 2,4,6-tris(benzylamino)-1,3,5-triazine at 58.8% and 2-dibenzylamino-4,6-bis(n-butylamino)-1,3,5-triazine at 3.1%.

Example 5

A 50-mL stainless steel autoclave was charged with 1.26 g (10.0 mmol.) of melamine, 400 mg of 5-% Pd-carried active carbon, 3.37 g (30.0 mmol.) of cyclohexanecarboxaldehyde and 15 mL of 1,4-dioxane. After the inside of the system was fully charged with a nitrogen gas, the reaction was conducted at a reaction temperature of 180° C. for six hours and under a hydrogen gas (initial pressure of 50 kg/cm$^2$). After the completion of the reaction, unreacted melamine was determined. As a result, the conversion ratio of the starting materials was 99.5%. After the catalysts and unreacted melamine were separated from the reaction solution through filtration, the solvent was distilled off to obtain crude reaction products. As a result that the reaction products were analyzed, the following were produced at the respective yields:

2,4-diamino-6-cyclohexylmethylamino-1,3,5-triazine at 7.5%, 2-amino-4,6-bis(cyclohexylmethylamino)-1,3,5-triazine at 30.1%, and 2,4,6-tris(cyclohexylmethylamino)-1,3,5-triazine at 61.3%.

Example 6

A 50-mL stainless steel autoclave was charged with 1.26 g (10.0 mmol.) of melamine, 205 mg of 5%-Rh-carried active carbon, 3.37 g (30.0 mmol.) of cyclohexanecarboxaldehyde and 15 mL of 1,4-dioxane. After the inside of the system was fully purged with a nitrogen gas, the reaction was conducted at a reaction temperature of 180° C. for ten hours and under a hydrogen gas (initial pressure of 70 kg/cm$^3$). After the completion of the reaction, unreacted melamine was determined. As a result, the conversion ratio of the starting materials was 25.5%. After the catalysts and unreacted melamine were separated from the reaction solution through filtration, the solvent was distilled off to obtain crude reaction products. As a result that the reaction products were analyzed, the following were produced at the respective yields:

2,4-diamino-6-cyclohexylmethylamino-1,3,5-triazine at 11.2%, 2-amino-4,6-bis(cyclohexylmethylamino)-1,3,5-triazine at 3.3%, 2,4,6-tris(cyclohexylmethylamino)-1,3,5-triazine at 3.0%

Example 7

A 50-mL stainless steel autoclave was charged with 1.26 g (10.0 mmol.) of melamine, 200 mg of 2-% Pt-carried active carbon, 3.37 g (30.0 mmol.) of cyclohexanecarboxaldehyde and 12 mL of 1,4-dioxane. After the inside of the system was fully purged with a nitrogen gas, the reaction was conducted at a reaction temperature of 180° C. for five hours and under a hydrogen gas (initial pressure of 50 kg/cm$^2$), while supplying hydrogen gas so as to keep the pressure during the reaction. After the completion of the reaction, unreacted melamine was determined. As a result, the conversion ratio of the starting materials were 5.9%. After the catalysts and unreacted melamine were separated from the reaction solution through filtration, the solvent was distilled off to obtain crude reaction products. As a result that the reaction products were analyzed, the following were produced at the respective yields:

2,4-diamino-6-cyclohexylmethylamino-1,3,5-triazine at 6.6%, and 2-amino-4,6-bis(cyclohexylmethylamino)-1,3,5-triazine at 0.8%.

Example 8

A 50-mL stainless steel autoclave was charged with 1.26 g (10.0 mmol.) of melamine, 200 mg of 5-% Ru-carried active carbon, 3.37 g (30.0 mmol.) of cyclohexanecarboxaldehyde and 12 mL of 1,4-dioxane. After the inside of the system was fully purged with a nitrogen gas, the reaction was conducted at a -reaction temperature of 180° C. for five hours and under a hydrogen gas (initial pressure of 50 kg/cm$^2$) while supplying hydrogen gas so as to keep the pressure during the reaction. After the completion of the reaction, unreacted melamine was determined. As a result, the conversion ratio of the starting materials were 19.6%. After the catalysts and unreacted melamine were separated from the reaction solution through filtration, the solvent was distilled off to obtain crude reaction products. As a result that the reaction products were analyzed, the following were produced at the respective yields:

2,4-diamino-6-cyclohexylmethylamino-1,3,5-triazine at 11.5%, and 2-amino-4,6-bis(cyclohexylmethylamino)-1,3,5-triazine at 3.1%.

Example 9

A 60-mL stainless steel autoclave was charged with 1.26 g (10.0 mmol.) of melamine, 192 mg of triruthenium dodecacarbonyl, 5.88 g (60.0 mmol.) of cyclohexanone and 20 mL. of 1,4-dioxane. After the inside of the system was fully purged with a nitrogen gas, the reaction was conducted at a reaction temperature of 180° C. for eleven hours and under a synthesized (H$_2$/CO=1/1)(initial pressure of 50 kg/cm$^2$). After the completion of the reaction, unreacted melamine was determined. As a result, the conversion ratio of the starting materials was 23.3%. After cooling, unreacted melamine was separated from the reaction solution through filtration, thus solvent was distilled off to obtain crude reaction products. As a result that the reaction products were analyzed, the following were produced at the respective yields:

2,4-diamino-6-cyclohexylamino-1,3,5-triazine at 6.8%, 2-amino-4,6-bis(cyclohexylamino)-1,3,5-triazine at 7.8%, and 2,4,6-tris(cyclohexylamino)-1,3,5-triazine at 4.4%.

Example 10

A 60-mL stainless steel autoclave was charged with 1.26 g (10.0 mmol.) of melamine, 408 mg of 5-% Pd-carried active carbon, 11.7 g (120.0 mmol.) of cyclohexanone and 15 mL of 1,4-dioxane. After the inside of the system was fully purged with a nitrogen gas, the reaction was conducted at a reaction temperature of 180° C. for two and half hours and under a hydrogen gas (initial pressure of 50 kg/cm$^2$). After the completion of the reaction, unreacted melamine was determined. As a result, the conversion ratio of the starting materials was 69.3% After cooling, the catalysts and unreacted melamine were separated from the reaction solution through filtration and the solvent was distilled off to obtain crude reaction products. As a result that the reaction products were analyzed, the following were produced at the respective yields:

2,4-diamino-6-cyclohexylamino-1,3,5-triazine at 19.8%, 2-amino-4,6-bis(cyclohexylamino)-1,3,5-triazine at 31.9%, 2,4,6-tris(cyclohexylamino)-1,3,5-triazine at 16.0%.

Example 11

A 100-mL stainless steel autoclave was charge with 1.26 g (10.0 mmol.) of melamine, 408 mg of 5-% Pd-carried active carbon, 11.7 g (120.0 mmol.) of cyclohexanone and 40 mL of ethanol. After the inside of the system was fully purged with a nitrogen gas, the reaction was conducted at a reaction temperature of 180° C. for eight and half hours and under a hydrogen gas (initial pressure of 50 kg/cm$^2$). After the completion of the reaction, catalyst and unreacted melamine were determined. As a result, the conversion ratio of the starting materials was 98.3%. After cooling, unreacted melamine was separated from the reaction solution through filtration and the solvent: was distilled off to obtain crude reaction products. As a result that the reaction products were analyzed, the following were produced at the respective yields:

2,4-diamino-6-cyclohexylamino-1,3,5-triazine at 4.5%, 2-amino-4,6-bis(cyclohexylamino)-1,3,5-triazine at 27.6% and 2,4,6-tris(cyclohexylamino)-1,3,5-triazine at 60.0%.

Example 12

A 40-mL stainless steel autoclave was charged with 1.87 g (10.0 mmol.) of benzoguanamine, 408 mg of 5-% Pd-carried active carbon, 2.16 g (30 mmol.) of n-butyraldehyde and 15 mL of ethanol. After the inside of the system was fully purged with a nitrogen gas, the reaction was conducted at a reaction temperature of 180° C. for ten hours and under a hydrogen gas (initial pressure of 50 kg/cm$^2$). After the completion of the reaction, unreacted starting materials were determined. As a result, the conversion ratio of the starting materials was 92.5%. As a result that the reaction products were analyzed, the following were produced at the respective yields:

2-amino-4-n-butylamino-6-phenyl-1,3,5-triazine at 37.0% and 2,4-bis(n-butylamino)-6-phenyl-1,3,5-triazine at 51.5%.

Example 13

A 38-mL stainless steel autoclave was charged with 1.40 g (10.0 mmol.) of 2-amino-4-methyl-6-methoxy-1,3,5-triazine, 204 mg of 5-% Pd-carried active carbon, 2.00 g (20.0 mmol.) of 1-hexanal and 15 mL of 1-hexanol. After the inside of the system was fully purged with a nitrogen gas, the reaction was conducted at a reaction temperature of 200° C. for twenty hours and under a hydrogen gas (initial pressure of 50 kg/cm$^2$). After the completion of the reaction, unreacted starting materials were determined. As a result, the conversion ratio of the starting materials was 88.0%. As a result that the reaction product were analyzed, 2-n-hexylamino-4-methyl-6-methoxy-1,3,5-triazine was obtained at a yield of 67.0%.

Example 14

A 100-mL stainless steel autoclave was charged with 3.64 g (20.0 mmol.) of 2-N-butylmelamine, 408 mg of 5-% Pd-carried active carbon, 4.32 g (60.0 mmol.) of n-butyraldehyde and 30 mL of 1-butanol. After the inside of the system was fully purged with a nitrogen gas, the reaction was conducted at a reaction temperature of 180° C. for six and half hours and under a hydrogen gas (initial pressure of 50 kg/cm$^2$). After the completion of the reaction, unreacted starting materials were determined. As a result, the conversion ratio of the starting materials was 96.5%. As a result that the reaction products were analyzed, the following were produced at the respective yields:

2,4-bis(n-butylamino)-6-amino-1,3,5-triazine at 14.7% and 2,4,6-tris(n-butylamino)-1,3,5-triazine at 77.0%.

Example 15

A 100-mL stainless steel autoclave was charged with 4.76 g (20.0 mmol.) of 2,4-bis(n-butylamino)-6-amino-1,3,5-triazine, 408 mg of 5-% Pd-carried active carbon, 2.16 g (30 mmol.) of n-butyraldehyde and 30 mL of 1-butanol. After the inside of the system was fully purged with a nitrogen gas, the reaction was conducted at a reaction temperature of 180° C. for two hours and under a hydrogen gas (initial pressure of 50 kg/cm$^2$), while supplying hydrogen so as to keep the pressure. After the completion of the reaction, unreacted starting materials were determined. As a result, the conversion ratio of the starting materials was 96.0%. As a result that the reaction products were analyzed, 2,4-6-tris(n-butylamino)-1,3,5-triazine was produced at the yield of 87.5%.

Example 16

A 100-mL stainless steel autoclave was charged with 4.76 g (20.0 mmol.) of 2-dibutylamino-4,6-diamino-1,3,5-triazine, 408 mg of 5-% Pd-carried active carbon, 4.32 g (60.0 mmol.) of n-butyraldehyde and 30 mL of 1-butanol. After the inside of the system was fully purged with a nitrogen gas, the reaction was conducted at a reaction temperature of 190° C. for one and half hours and under a hydrogen gas (initial pressure of 50 kg/cm$^2$). After the completion of the reaction, unreacted starting materials were determined. As a result, the conversion ratio of the starting materials was 92.6%. As a result that the reaction products were analyzed, the following were produced at the respective yields:

2-di-n-butylamine-4-butylamino-6-amino-1,3,5-triazine at 16.0% and 2-di-n-butyl-4,6-bis(n-butylamino)-1,3,5-triazine at 69.4%.

Example 17

A 100-mL stainless steel autoclave was charged with 3.64 g (20.0 mmol.) of 2-N-butylmelamine, 63.9 mg (0.1 mmol.) of triruthenium dodecacarbonyl, 2.16 g (30.0 mmol.) of n-butyraldehyde and 30 mL of 1-butanol. After the inside of the system was fully purged with a nitrogen gas, a synthesized gas (H$_2$/CO=2/1) was introduced at the initial pressure of 100 kg/cm$^2$. After the reaction temperature was raised to 200° C., the reaction was conducted for two hours, while supplying a hydrogen gas to keep the presssure. After the completion of the reaction, unreacted starting materials were determined. As a result, the conversion ratio of the starting materials was 45.3%. As a result that the reaction products were analyzed, the following were produced at the respective yields:

2,4-bis(n-butylamino)-6-amino-1,3,5-triazine at 12.1% and 2,4,6-tris(n-butylamino)-1,3,5-triazine at 25.4%.

Example 18

A 100-mL stainless steel autoclave was charged with 3.64 g (20.0 mmol.) of 2-diethylamino-4,6-diamino-1,3,5-triazine, 408 mg of 5-% Pd-carried active carbon, 4.32 g (60.0 mmol.) of n-butyraldehyde and 30 mL of 1-butanol. After the inside of the system was fully purged with a nitrogen gas, the reaction was conducted at a reaction temperature of 200° C. for two hours and under a hydrogen gas (initial pressure of 30 kg/cm$^2$). After the completion of the reaction, unreacted starting materials were determined. As a result, the conversion ratio of the starting materials was 91.9%. As a result that the reaction products were analyzed, the following were produced at the respective yields:

2-diethylamino-4-n-butylamino-6-amino-1,3,5-triazine at 13.8% and 2-diethylamino-4,6-bis(n-butylamino)-1,3,5-triazine at 68.5%.

Example 19

A 40-mL stainless steel autoclave was charged with 1.96 g (10.0 mmol.) of 2-morpholino-4,6-diamino-1,3,5-triazine, 204 mg of 5-% Pd-carried active carbon, 3.00 (30.0 mmol.) of 1-hexanal and 20 mL of 1-hexanol. After the inside of the system was fully purged with a nitrogen gas, the reaction was conducted at a reaction temperature of 200° C. for ten hours and under a hydrogen gas (initial pressure of 50 kg/cm$^2$). After the completion of the reaction, unreacted starting materials were determined. As a result, the conversion ratio of the starting materials was 95.4%. As a result that the reaction products were analyzed, the following were produced at the respective yields:

2-morpholino-4-n-butylamino-6-amino-1,3,5-triazine at 9.8% and 2-morpholino-4,6-bis(n-butylamino)-1,3,5-triazine at 81.4%.

Example 20

A 60-mL stainless steel autoclave was charged with 1.26 g (10.0 mmol.) of melamine, 200 mg of 5-% Pd-carried active carbon, 0.72 g (10.0 mmol.) of n-butyraldehyde and 20 mL of 1,4-dioxane. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 47.7%. After the catalyst and unreacted melamine were separated from the reaction solution through filtration, the solvent was distilled off to obtain crude reaction products. As a result that the reaction products were analyzed, the following were produced at the respective yields:

2,4-diamino-6-n-butylamino-1,3,5-triazine at 23.2%, 2-amino-4,6-bis(n-butylamino)-1,3,5-triazine at 18.5% and 2,4,6-tris(n-butylamino)-1,3,5-triazine at 10.0%.

Example 21

A 60-mL stainless steel autoclave was charged with 1.26 g (10.0 mmol.) of melamine, 200 mg of 5-% Pd-carried active carbon, 1.44 g (20.0 mmol.) of n-butyraldehyde and 20 mL of 1,4-dioxane. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 82.7%. After the catalyst and unreacted melamine were separated from the reaction solution through filtration, the solvent was distilled off to obtain crude reaction products. As a result that the reaction products were analyzed, the following were produced at the respective yields:

2,4-diamino-6-n-butylamino-1,3,5-triazine at 25.8%, 2-amino-4,6-bis(n-butylamino)-1,3,5-triazine at 32.4% and 2,4,6-tris(n-butylamino)-1,3,5-triazine at 21.6%.

Example 22

A 60-mL stainless steel autoclave was charged with 1.26 g (10.0 mmol.) of melamine, 200 mg of 5-% Pd-carried active carbon, 2.16 g (30.0 mmol.) of n-butyraldehyde and 20 mL of 1,4-dioxane. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 98.8%. After the catalyst and unreacted melamine were separated from the reaction solution through filtration, the solvent was distilled off to obtain crude reaction products. As a result that the reaction products were analyzed, the following were produced at the respective yields:

2,4-diamino-6-n-butylamino-1,3,5-triazine at 8.6%, 2-amino-4,6-bis(n-butylamino)-1,3,5-triazine at 33.4% and 2,4,6-tris(n-butylamino)-1,3,5-triazine at 51.3%.

Example 23

A 60-mL stainless steel autoclave was charged with 1.26 g (10.0 mmol.) of melamine, 200 mg of 5-% Pd-carried active carbon, 4.32 g (60.0 mmol.) of n-butyraldehyde and 20 mL of 1,4-dioxane. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 99.9%. After the catalyst and unreacted melamine were separated from the reaction solution through filtration, the solvent was distilled off to obtain crude products of the reaction product. As a result that the reaction products were analyzed, the following were produced at the respective yields:

2,4-diamino-6-n-butylamino-1,3,5-triazine at 0.1%, 2-amino-4,6-bis(n-butylamino)-1,3,5-triazine at 0.9%, 2,4,6-tris(n-butylamino)-1,3,5-triazine at 75.6%.

2,4-bis(n-butylamino)-6-di-n-butylamino-1,3,5-triazine at 21.6% and 2,4-bis(di-n-butylamino)-6-n-butylamino-1,3,5-triazine at 1.1%.

Example 24

A 60-mL stainless steel autoclave was charged with 1.26 g (10.0 mmol.) of melamine, 200 mg of 5-% Pd-carried active carbon, 7.20 g (100.0 mmol.) of n-butyraldehyde and 20 mL of 1,4-dioxane. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 100%. After the catalyst and unreacted melamine were separated from the reaction solution through filtration, the solvent was distilled off to obtain crude reaction products. As a result that the reaction products were analyzed, the following were produced at the respective yields:

2,4,6-tris(n-butylamino)-1,3,5-triazine at 67.0%.

2,4-bis(n-butylamino)-6-di-n-butylamino-1,3,5-triazine at 29.3% and 2,4-bis(di-n-butylamino)-6-n-butylamino-1,3,5-triazine at 2.7%.

Example 25

A 60-mL stainless steel autoclave was charged with 1.26 g (10.0 mmol.) of melamine, 200 mg of 5-% Pd-carried active carbon, 2.16 g (30.0 mmol.) of n-butyraldehyde and 20 mL of ethanol. After the inside of the system was fully purged with a nitrogen gas, the reaction was conducted at a reaction temperature of 180° C. for six hours and under a hydrogen gas (initial pressure of 40 kg/cm$^2$). After the completion of the reaction, unreacted melamine was determined. As a result, the conversion ratio of the starting materials was 97.2%. After the catalyst and unreacted melamine were separated from the reaction solution through filtration, the solvent was distilled off to obtain crude reaction products. As a result that the reaction products were analyzed, the following were produced at the respective yields:

2,4-diamino-6-n-butylamino-1,3,5-triazine at 9.6%, 2-amino-4,6-bis(n-butylamino)-1,3,5-triazine at 24.5%, 2,4,6-tris(n-butylamino)-1,3,5-triazine at 53.9% and 2,4-bis(n-butylamino)-6-di-n-butylamino-1,3,5-triazine at 7.0%.

Example 26

A 60-mL stainless steel autoclave was charged with 1.26 g (10.0 mmol.) of melamine, 200 mg of 5-% Pd-carried active carbon, 4.32 g (60.0 mmol.) of n-butyraldehyde and 20 mL of ethanol. After the inside of the system was fully purged with a nitrogen gas, the reaction was conducted at a reaction, temperature of 180° C. for six hours and under a hydrogen gas (initial pressure of 40 kg/cm$^2$). After the completion of the reaction, unreacted melamine was determined. As a result, the conversion ratio of the starting materials was 99.5%. After the catalyst and unreacted melamine were separated from the reaction solution through filtration, the solvent was distilled off to obtain crude reaction products. As a result that the reaction products were analyzed, the following were produced at the respective yields:

2,4,6-tris(n-butylamino)-1,3,5-triazine at 56.5%.

2,4-bis(n-butylamino)-6-di-n-butylamino-1,3,5-triazine at 31.1% and 2,4-bis(di-n-butylamino)-6-n-butylamino-1,3,5-triazine at 10.0%.

Example 27

A 60-mL stainless steel autoclave was charged with 1.26 g (10.0 mmol.) of melamine, 148 mg of Raney nickel catalyst 2.16 g (30.0 mmol.) of n-butyraldehyde and 20 mL of methanol. After the inside of the system was fully purged with a nitrogen gas, the reaction was conducted at a reaction temperature of 200° C. for one hour and under a hydrogen gas (initial pressure of 50 kg/cm$^2$). After the completion of the reaction, unreacted melamine was determined. As a result, the conversion ratio of the starting materials was 25.4%. After cooling, the catalyst and unreacted melamine were separated from the reaction solution through filtration and the solvent was distilled off to obtain crude reaction products. As a result that the reaction products were analyzed, the following were produced at the respective yields:

2,4-diamino-6-n-butylamino-1,3,5-triazine at 15.6% and
2-amino-4,6-bis(n-butylamino)-1,3,5-triazine at 3.1%, Example 28

A 60-mL stainless steel autoclave was charged with 1.26 g (10.0 mmol.) of melamine, 25.0 mg of nickel-diatomaceous earth catalyst, 2.16 g (30.0 mmol.) of n-butyraldehyde and 20 mL of methanol. After the inside of the system was fully purged with a nitrogen gas, the reaction was conducted at a reaction temperature of 200° C. for six hours and under a hydrogen gas (initial pressure of 50 kg/cm$^2$). After the completion of the reaction, unreacted melamine was determined. As a result, the conversion ratio of the starting materials was 78.2%. After the catalyst and unreacted melamine were separated from the reaction solution through filtration, the solvent was distilled off to obtain crude reaction products. As a result that the reaction products were analyzed, the following were produced at the respective yields:

2,4-diamino-6-n-butylamino-1,3,5-triazine at 27.8%,
2-amino-4,6-bis(n-butylamino)-1,3,5-triazine at 6.9%,
2,4,6-tris(n-butylamino)-1,3,5-triazine at 2.5% and
2,4-bis(n-butylamino)-6-di-n-butylamino-1,3,5-triazine at 1.0%.

Example 29

A 60-mL stainless steel autoclave was charged with 1.26 g (10.0 mmol.) of melamine, 408.0 mg of 5-% Pd-carried active carbon, 6.96 g (0.12 mmol.) of acetone and 20 mL of ethanol. After the inside of the system was fully purged with a nitrogen gas, the reaction was conducted at a reaction temperature of 180° C. for six hours and under a hydrogen gas (initial pressure of 50 kg/cm$^2$). After the completion of the reaction, unreacted melamine was determined. As a result, the conversion ratio of the starting materials was 98.0%. After the catalyst and unreacted melamine were separated from the reaction solution through filtration, the solvent was distilled off to obtain crude reaction products. As a result that the reaction products were analyzed, the following were produced at the respective yields:

2,4-diamino-6-isopropylamino-1,3,5-triazine at 31.9%,
2-amino-4,6-bis(isopropylamino)-1,3,5-triazine at 42.0%,
2,4,6-tris(isopropylamino)-1,3,5-triazine at 13.6% and
2,4-bis(isopropylamino)-6-diisopropylamino-1,3,5-triazine at 1.3%.

Industrial Availability

According to the process of the present invention, substituted 1,3,5-triazine derivatives can be easily obtained from amino-triazines of the formula (I) in high yields under relatively moderate reaction conditions. These substituted-1,3,5-triazine derivatives are useful compounds that find wide acceptance in intermediates of fine chemicals such as agricultural chemicals, medications, dyestuffs, paints and the like and in resin materials and flame-retardant materials.

The substituted 1,3,5-triazine derivatives which are alkylated by the method of the present invention are generally obtained in mixture form. However, these products can be separated in pure form by methods for generally separating organic compounds and be applied to various uses as mentioned above.

Further, many of the substituted triazines obtained by the reaction of the present invention have been relatively hard to produce so far, and are therefore interesting in terms of solubility in water or various organic solvents, stability at high temperatures, melting point, boiling point and basicity.

Accordingly, these compounds are considered to find wider acceptance than before.

We claim:

1. A method of alkylation of 1,3,5-triazine compounds comprising reacting a 1,3,5-triazine compound of the formula (I) having at least one or more amino groups or mono-substituted amino groups on a carbon atom of the ring in the presence of a catalyst of a metal of group VIII in the periodic table and a hydrogen-containing gas to alkylate at least one or more amino groups or mono-substituted amino groups

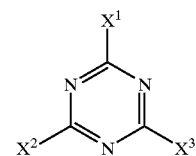

(I)

wherein at least one of $X^1$, $X^2$ and $X^3$ independently represents $NHR^1$ in which $R^1$ represents a hydrogen atom or a $C_{1-20}$ alkyl group that is optionally substituted with a hydroxyl group, a $C_{1-6}$ alkoxy group or a phenyl group, $X^1$, $X^2$ and $X^3$ which are not $NHR^1$ independently represent $NR^2R^3$ in which $R^2$ and $R^3$ independently represent a $C_{1-20}$ alkyl group wherein said alkyl group is optionally substituted with a hydroxyl group, a $C_{1-6}$alkoxy group or phenyl group, $R^2$ and $R^3$ may together form —(CH$_2$)$_{2-5}$—, CH$_2$CH$_2$—(C$_{1-8}$ alkyl)N—CH$_2$CH$_2$— or CH$_2$CH$_2$—O—CH$_2$CH$_2$— in which an alkylene chain is desirably substituted with one or two $C_{1-8}$ alkyl groups), a $C_{1-20}$ alkyl group, a phenyl group or a $C_{1-10}$ alkoxy group, with aldehydes or ketones of the formula (II)

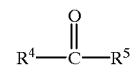

(II)

wherein $R^4$ and $R^5$ independently represent a hydrogen atom or a $C_{1-20}$ alkyl group that is optionally substituted with a hydroxyl group, a $C_{1-6}$ alkoxy group or a phenyl group, or $R^2$ and $R^3$ may together form an alkylene group: —(CH$_2$)$_{3-5}$—.

2. A method of alkylation of 1,3,5-triazine derivatives in which substituted 1,3,5-triazine derivatives obtained by the method of alkylation as claimed in claim 1 are substituted 1,3,5-triazine derivatives of the formula (III)

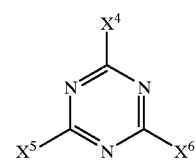

(III)

wherein at least one of $X^4$, $X^5$ and $X^6$ independently represents $NR^6R^7$ in which $R^6$ and $R^7$ independently represent a hydrogen atom (provided that a case where $R^6$ and $R^7$ of $X^4$, $X^5$ and $X^7$ are all hydrogen atoms is excluded) or a $C_{1-20}$ alkyl group that is optionally substituted with a hydroxyl group, a $C_{1-6}$ alkoxy group or a phenyl group or $R^2$ and $R^3$ together form —(CH$_2$)$_{2-5}$—, —CH$_2$CH$_2$—(C$_{1-8}$ alkyl)N—CH$_2$CH$_2$— or —CH$_2$CH$_2$—O—

$CH_2CH_2$— in which an alkylene chain is desirably substituted with one or two $C_{1-8}$ alkyl groups, $X^4$, $X^5$ and $X^6$ which are not $NR^6R^7$ independently represent a $C_{1-20}$ alkyl group, a phenyl group or a $C_{1-10}$ alkoxy group.

3. The method of alkylation of 1,3,5-triazine derivatives of claim 1, wherein the catalyst of a metal of group VIII in the periodic table is at least one of catalysts selected from cobalt, nickel, ruthenium, rhodium, palladium, osmium, iridium and platinum.

4. The method of alkylation of 1,3,5-triazine derivatives of claim 3, wherein the catalyst of a metal of group VIII in the periodic table is at least one of catalysts selected from cobalt, nickel, ruthenium, rhodium, palladium and platinum.

5. The method of alkylation of 1,3,5-triazine derivatives of claim 4, wherein the catalyst of a metal of group VIII in the periodic table is at least one of catalysts selected from nickel, ruthenium, palladium and platinum.

6. The method of alkylation of 1,3,5-triazine derivatives of claim 3, wherein the catalysts are complex catalysts.

7. The method of alkylation of 1,3,5-triazine derivatives of claim 4, wherein the catalysts are complex catalysts.

8. The method of alkylation of 1,3,5-triazine derivatives of claim 5, wherein the catalysts are complex catalysts.

9. A method of alkylation of 1,3,5-triazine derivatives of claim 3, wherein the catalysts are elements-carried catalysts.

10. A method of alkylation of 1,3,5-triazine derivatives of claim 4, wherein the catalysts are elements-carried catalysts.

11. A method of alkylation of 1,3,5-triazine derivatives of claim 5, wherein the catalysts are elements-carried catalysts.

12. A method of alkylation of 1,3,5-triazine derivatives of claim 9, wherein carriers of the elements-carried catalyst are silica, alumina, zeolite and carbon.

13. A method of alkylation of 1,3,5-triazine derivatives of claim 10, wherein carriers of the elements-carried catalyst are silica, alumina, zeolite and carbon.

14. A method of alkylation of 1,3,5-triazine derivatives of claim 11, wherein carriers of the elements-carried catalyst are silica, alumina, zeolite and carbon.

* * * * *